(12) United States Patent
Baker et al.

(10) Patent No.: US 9,622,892 B2
(45) Date of Patent: Apr. 18, 2017

(54) LONGITUDINALLY REINFORCED SHEATH

(71) Applicant: Cook Medical Technologies LLC, Bloomington, IN (US)

(72) Inventors: Brett O. Baker, Ellettsville, IN (US); Carrie L. Fercik Grant, Ellettsville, IN (US); James C. Merk, Terre Haute, IN (US); Scott E. Boatman, Bloomington, IN (US); David A. Drewes, Jr., Bloomington, IN (US); Michael D. Deckard, Solsberry, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 257 days.

(21) Appl. No.: 13/788,469

(22) Filed: Mar. 7, 2013

(65) Prior Publication Data
US 2013/0289697 A1    Oct. 31, 2013

Related U.S. Application Data

(60) Provisional application No. 61/638,827, filed on Apr. 26, 2012.

(51) Int. Cl.
*A61F 2/962* (2013.01)
*A61M 25/00* (2006.01)
*A61M 25/06* (2006.01)

(52) U.S. Cl.
CPC ........... *A61F 2/962* (2013.01); *A61M 25/005* (2013.01); *A61M 25/0012* (2013.01);
(Continued)

(58) Field of Classification Search
CPC .. A61F 2/95; A61F 2/962; A61F 2/966; A61F 2/2427; A61F 2/2436;
(Continued)

(56) References Cited

U.S. PATENT DOCUMENTS 3,585,707 A    6/1971  Stevens
4,176,662 A   12/1979  Frazer
(Continued)

FOREIGN PATENT DOCUMENTS

EP    0 879 585 A1    5/1998
EP      2301617 A1    3/2011
WO    WO 00/43061    7/2000

OTHER PUBLICATIONS

International Search Report and Written Opinion of the International Searching Authority, dated Jun. 21, 2013, pp. 1-11, International Application No. PCT/US2013/038115, European Patent Office, Rijswijk, the Netherlands.
(Continued)

*Primary Examiner* — Todd J Scherbel
(74) *Attorney, Agent, or Firm* — Brinks Gilson & Lione; Eric Babych; John C. Bacoch (57) ABSTRACT

A sheath for deploying a medical device to a target site in the body of a patient. A tubular inner liner has a proximal portion, a distal portion, and an outer surface. An outer jacket has a proximal portion, a distal portion, and an inner surface. A reinforcing member is received within a length of the outer jacket. The outer jacket is positioned longitudinally around the inner liner and bonded to the outer surface of the liner. The reinforcing member, which may be a triaxial braid, or an encapsulated longitudinal reinforcing wire, extends along the outer jacket length and is configured for inhibiting elongation of the sheath upon deployment of the device.

12 Claims, 3 Drawing Sheets

(52) U.S. Cl.
CPC .... *A61M 25/0045* (2013.01); *A61M 25/0052* (2013.01); *A61M 25/0053* (2013.01); *A61M 25/0662* (2013.01); *A61M 2025/0063* (2013.01)

(58) Field of Classification Search
CPC .......... A61F 2/2466; A61F 2002/0072; A61M 25/0012; A61M 25/0045; A61M 25/005; A61M 25/0052; A61M 25/0053; A61M 25/0662; A61M 2025/0046; A61M 2025/0047; A61M 2025/0048
See application file for complete search history.

(56) References Cited

U.S. PATENT DOCUMENTS

| | | | |
|---|---|---|---|
| 4,777,955 A | 10/1988 | Brayton et al. | |
| 4,945,920 A | 8/1990 | Clossick | |
| 4,979,956 A | 12/1990 | Silvestrini | |
| 5,019,057 A | 5/1991 | Truckai | |
| 5,188,872 A | 2/1993 | Quigley | |
| 5,380,304 A | 1/1995 | Parker | |
| 5,397,365 A | 3/1995 | Trentacosta | |
| 5,718,159 A | 2/1998 | Thompson | |
| 5,758,562 A | 6/1998 | Thompson | |
| 5,792,124 A | 8/1998 | Horrigan et al. | |
| 6,152,912 A * | 11/2000 | Jansen et al. | 604/526 |
| 6,287,329 B1 | 9/2001 | Duerig et al. | |
| 6,332,465 B1 | 12/2001 | Xue et al. | |
| 6,425,898 B1 | 7/2002 | Wilson et al. | |
| 6,709,429 B1 * | 3/2004 | Schaefer et al. | 604/527 |
| 6,726,712 B1 | 4/2004 | Raeder-Devens et al. | |
| 6,939,337 B2 | 9/2005 | Parker et al. | |
| 6,942,688 B2 | 9/2005 | Bartholf et al. | |
| 7,052,513 B2 | 5/2006 | Thompson | |
| 7,452,374 B2 | 11/2008 | Hain et al. | |
| 7,641,681 B2 | 1/2010 | Sherry et al. | |
| 7,780,716 B2 | 8/2010 | Pappas et al. | |
| 8,075,528 B2 | 12/2011 | Widenhouse et al. | |
| 8,075,606 B2 | 12/2011 | Dorn | |
| 8,122,809 B2 | 2/2012 | Simpson | |
| 2001/0010247 A1 | 8/2001 | Snow | |
| 2001/0034514 A1 | 10/2001 | Parker | |
| 2004/0133264 A1 | 7/2004 | Moore | |
| 2008/0188928 A1 | 8/2008 | Salahieh et al. | |
| 2010/0049168 A1 | 2/2010 | Parker et al. | |
| 2010/0211153 A1 | 8/2010 | Cook et al. | |
| 2012/0310214 A1 * | 12/2012 | Hennessy | 604/527 |

OTHER PUBLICATIONS

International Preliminary Report on Patentability for PCT/2013/038115 dated Oct. 28, 2014, 7 pages.

* cited by examiner

LONGITUDINALLY REINFORCED SHEATH

RELATED APPLICATION

The present patent document claims the benefit of the filing date under 35 U.S.C. §119(e) of Provisional U.S. Patent Application Ser. No. 61/638,827, filed Apr. 26, 2012, which is hereby incorporated by reference.

BACKGROUND

1. Technical Field

This invention relates to the field of medical devices, and more particularly, to an elongated sheath having at least one reinforcing member extending along the length of the sheath.

2. Background Information

Numerous advances of considerable note have occurred in medical surgical techniques over the last few decades. Among the most significant advances has been the adoption, and now-routine performance, of a wide variety of minimally invasive procedures. Such minimally invasive procedures can be distinguished from conventional open surgical procedures in that access to a site of concern within a patient is achieved through a relatively small incision, into which a tubular device (such as a sheath) is inserted or introduced. The tubular sheath keeps the incision open while permitting access to the target site via the interior (i.e., lumen) of the sheath. Non-limiting examples of such devices include introducer sheaths, guide catheters, and like devices well known in the art (devices collectively referred to herein as "sheaths" or "introducer sheaths").

Body passageways in which medical interventional devices, such as stents, are now commonly introduced include the esophagus, trachea, colon, biliary tract, urinary tract, and vascular system, among other locations within the body. One particularly significant example of a minimally invasive technique involves the temporary or permanent implantation of a medical interventional device, such as a stent, into a passageway in the body of a patient.

When placing the medical interventional device, communication with the passageway is typically attained by initially inserting the distal end of an access device, such as an introducer sheath, into the body passageway. Since the introducer sheath must often traverse tortuous pathways to reach the target site, the sheath often includes a coil reinforcement to facilitate passage through the pathways without kinking. Examples of introducer sheaths of this type are described in U.S. Pat. No. 5,380,304, and U.S. Pat. Publ. No. 2001/0034514, both incorporated by reference herein. The sheaths described in these patents include a lubricious inner liner having a helical coil fitted over the liner. An outer tube is connected to the outer surface of the liner through the coil turns. The coil reinforcement imparts kink resistant to this thin-walled sheath through a wide range of bending.

Another example of an introducer sheath is provided in U.S. Pat. No. 5,792,124, incorporated by reference herein. This patent discloses an introducer sheath having a woven braid as a reinforcing member. Although braided and coiled structures are now routinely used as reinforcements in tubular medical devices, those skilled in the art recognize that these reinforcements are not generally considered interchangeable. Rather, each is typically utilized to address a particular condition likely to be of concern during introduction of the sheath into a body opening. For example, a coiled reinforcement is typically utilized in a sheath to minimize the possibility of the sheath kinking, and/or to minimize ovalization of the sheath lumen during bending of the sheath. On the other hand, a braid is utilized when it is desired to impart stiffness, pushability, or torqueability to the sheath. Such properties are advantageous when maneuvering a lengthy sheath or catheter into remote anatomy. A braid reinforcement is not generally capable of providing the type of kink resistance available with a coil. Similarly, a coil reinforcement is not generally capable of providing the type of pushability or torqueability available with a braid.

The medical interventional device, such as an expandable stent, etc., is deployed at the target site from a lumen in the introducer sheath. Typically, the device is positioned at the target site by withdrawing the introducer sheath from around the device while the device is in a constricted condition. An inner catheter may be provided in the sheath lumen for preventing the device from withdrawing with the sheath. Alternatively, the constricted device may be pushed from the distal end of the sheath by a pusher mechanism positioned in the sheath lumen. In either technique, upon deployment at the target site, the device expands to the diameter of the surrounding body passageway.

Deployment of expandable devices, such as stents, in this manner is now a routine practice, and such deployment may often be carried out with only a minimum of complications, if any. This is particularly true when such devices have a relatively short length (e.g., less than about 80 mm) and/or a relatively modest outer diameter. However, as medical technology has progressed, interventional devices having longer lengths (e.g., about 100 to 300 mm or more) and/or having outer coatings, coverings, etc., that increase the effective outer diameter of the device have become more common. When such devices are placed in a sheath lumen for delivery to the target site, the greater length and/or diameter of such devices increases the deployment forces necessary to extract the device from the sheath when compared to shorter and/or lesser diameter devices. This increase in deployment forces is due primarily to the increased outward forces exerted by the longer and/or greater diameter devices on the interior wall of the sheath.

In this event, an introducer sheath having a coiled reinforcement has a tendency to stretch longitudinally as it is withdrawn from around the interventional device. Although this phenomenon may also occur with non-coated, non-covered, or shorter interventional devices, it is more pronounced with the coated, covered, or longer diameter devices. With such coated, covered or longer diameter devices, the stretching of the sheath causes the distance between adjacent turns of the coil to increase. This longitudinal expansion of the reinforcing coil adversely affects the ability of the sheath wall to withstand the radial expansive forces exerted on the interior of the wall by the stent, which may result in pockets being formed in the sheath wall between adjacent coil turns. When this occurs, surfaces of the undeployed stent may expand into such pockets, thereby undesirably increasing the resistance imparted by the stent upon the sheath, and hindering efficient deployment of the stent. In addition, the sheath may elongate as it is withdrawn from the stent. When such elongation occurs, the distance the sheath handle travels is reduced, which may prevent the stent from being fully deployed in the vessel.

A sheath having a braid reinforcement is also prone to longitudinal stretching, or elongation, upon withdrawal from the stent, due to the increased deployment forces exerted on the sheath wall. With a braid reinforcement, such elongation reduces the inner diameter of the sheath to an extent that the stent cannot be efficiently extracted therefrom, if possible at all. Alternatively, such elongation may necessitate the use of a larger diameter sheath than desired, so that the stent can still be deployed therefrom in light of the expected elongation and reduction in diameter of the sheath upon use.

It is desired to provide an improved introducer sheath or similar apparatus suitable for traversing tortuous passageways in the patient's anatomy during delivery of a medical interventional device, such as an expandable stent. It is also desired to provide an introducer sheath that is capable of minimizing elongation or stretching during deployment of the sheath from the medical interventional device, thereby providing for more efficient deployment of the sheath when used to position the interventional device in a body passageway.

SUMMARY

The shortcomings of the prior art are addressed by the longitudinally reinforced sheath of the present invention. In one form thereof, the sheath includes a tubular liner having a proximal portion, a distal portion, and an outer surface. An outer jacket having a proximal portion, a distal portion, and an inner surface, is positioned longitudinally around the liner such that the outer jacket inner surface is bonded to the outer surface of the liner. A reinforcing member is received within a length of the outer jacket. The reinforcing member extends along the outer jacket length and is configured for inhibiting elongation of the sheath upon deployment of a medical device from the sheath.

In another form thereof, a longitudinally reinforced sheath includes a tubular inner liner having a proximal portion, a distal portion, and an outer surface. A reinforcing element disposed along the outer surface of the inner liner comprises a triaxial braid. The triaxial braid is disposed at the proximal portion of the inner liner and extends distally therefrom. An outer jacket is positioned longitudinally around the reinforcing element, and is connected to the inner liner.

In still another form thereof, a method is provided for forming an introducer sheath. An inner liner is positioned over a mandrel. An outer jacket having a longitudinal reinforcing member at least partially encapsulated along a length thereof is positioned over the inner liner. An assembly comprising the inner liner, reinforcing member, and outer jacket is heated such that the outer jacket at least partially melts and bonds to an outer surface of the inner liner.

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the sheath, as well as the axial ends of various component features. The term "proximal" is used in its conventional sense to refer to the end of the sheath (or component thereof) that is closest to the operator during use of the device. The term "distal" is used in its conventional sense to refer to the end of the sheath (or component thereof) that is initially inserted into the patient, or that is closest to the patient during use.

When conventional sheaths are used to deploy stents and other interventional devices having a relatively short length, such deployments may often be carried out without undue complication. The relatively short length of the interventional device, most of which are less than about 80 mm in length, typically provides minimal resistance to the interior of the sheath upon deployment.

When comparatively longer stents (e.g., greater than 100 mm in length) are deployed from prior art sheaths, however, the deployment of the stent from a sheath may be less than optimal. Due to the greater length of these stents, a greater aggregate outward force is exerted by the stent upon the interior wall of the sheath, when compared to the force exerted by a stent of a lesser length. As a result, a higher push force must typically be imparted by the inner catheter to overcome the tendency of the stent to remain with the sheath as the sheath is withdrawn from the passageway. This phenomenon may also occur upon the deployment of coated or covered stents from the sheath. This is due to the increased forces exerted against the wall of the sheath by the larger diameter coated stent when compared to an otherwise similar, but uncoated or uncovered stent.

The resistance imparted by the stent on the interior wall of the sheath upon deployment may cause the sheath to stretch in the longitudinal direction as the sheath is withdrawn from around the stent. Such stretching may have little practical significance when smaller stents are positioned within the sheath. However, with longer stents, the increased stent length results in greater radially outwardly directed forces exerted by the constricted stent within the sheath. As a sheath having a braid reinforcement is stretched, the braid constricts in diameter around the stent, thereby further increasing the outwardly directed forces. This action typically requires that an even greater pull force must be imparted on the sheath to overcome the tendency of the stent to remain with the sheath upon withdrawal of the sheath.

This phenomenon is not exclusive to the use of longer stents, and may occur when deploying stents less than about 100 mm in length. However, the effect is generally more pronounced with longer stents, and/or with coated or covered stents of any length wherein the additional diameter imparted to the stent by the coating/covering requires additional forces upon deployment. Furthermore, the effect typically increases with the length of the stent being deployed, and/or with the amount of the coating/covering. Thus, for example, the effect is generally more pronounced with a stent having a length of 200 mm when compared to a length of 100 mm; with a stent having a length of 300 mm when compared to a stent having a length of 200 mm, etc.

The inventive sheath is provided with a longitudinal reinforcement to inhibit elongation, or stretching, of the sheath. The longitudinal reinforcement may be woven into a braided reinforcement, or may otherwise be incorporated into the matrix or body of the sheath as further described in the examples hereinbelow.

Figure 1:
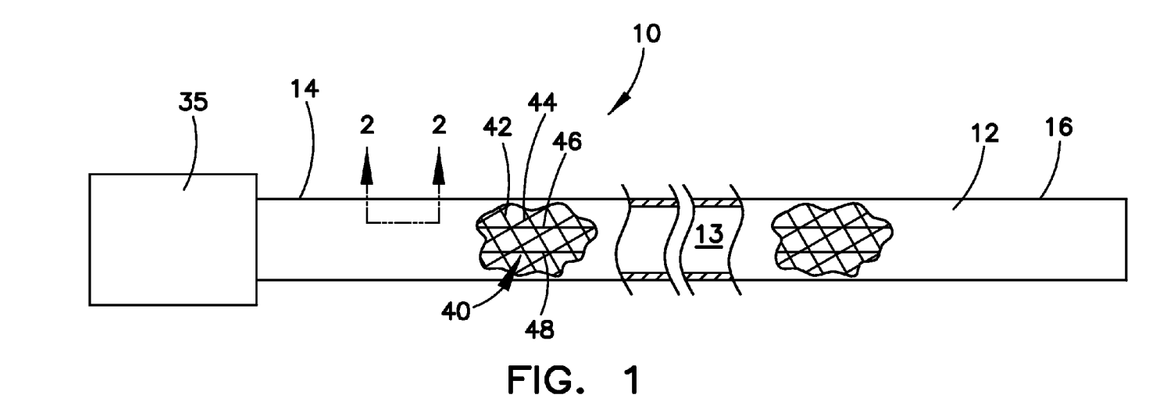
FIG. 1 is a side view, partially in section, illustrating a longitudinally reinforced sheath according to one embodiment of the present invention.
Figure 2:
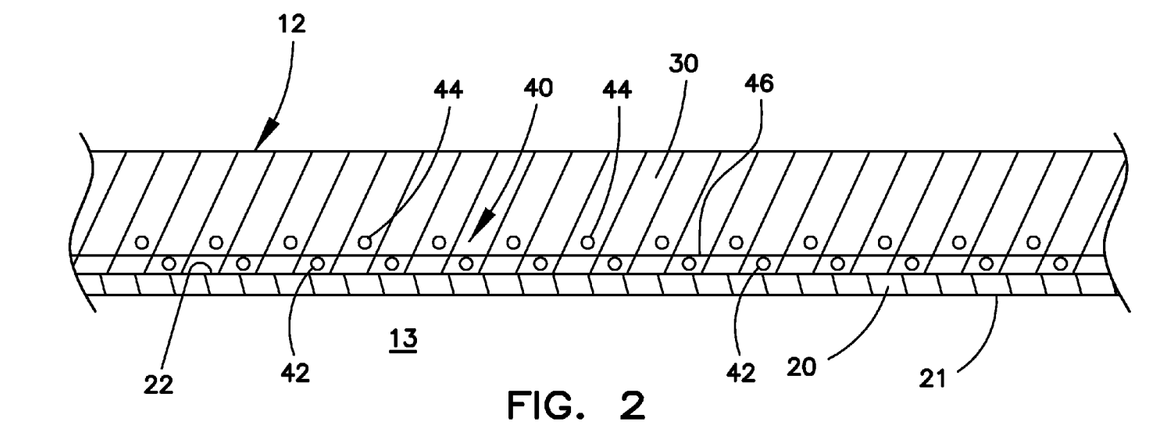
FIG. 2 is an enlarged longitudinal cross-sectional view of a portion of the wall of the longitudinally reinforced sheath of FIG. 1.
Figure 3:
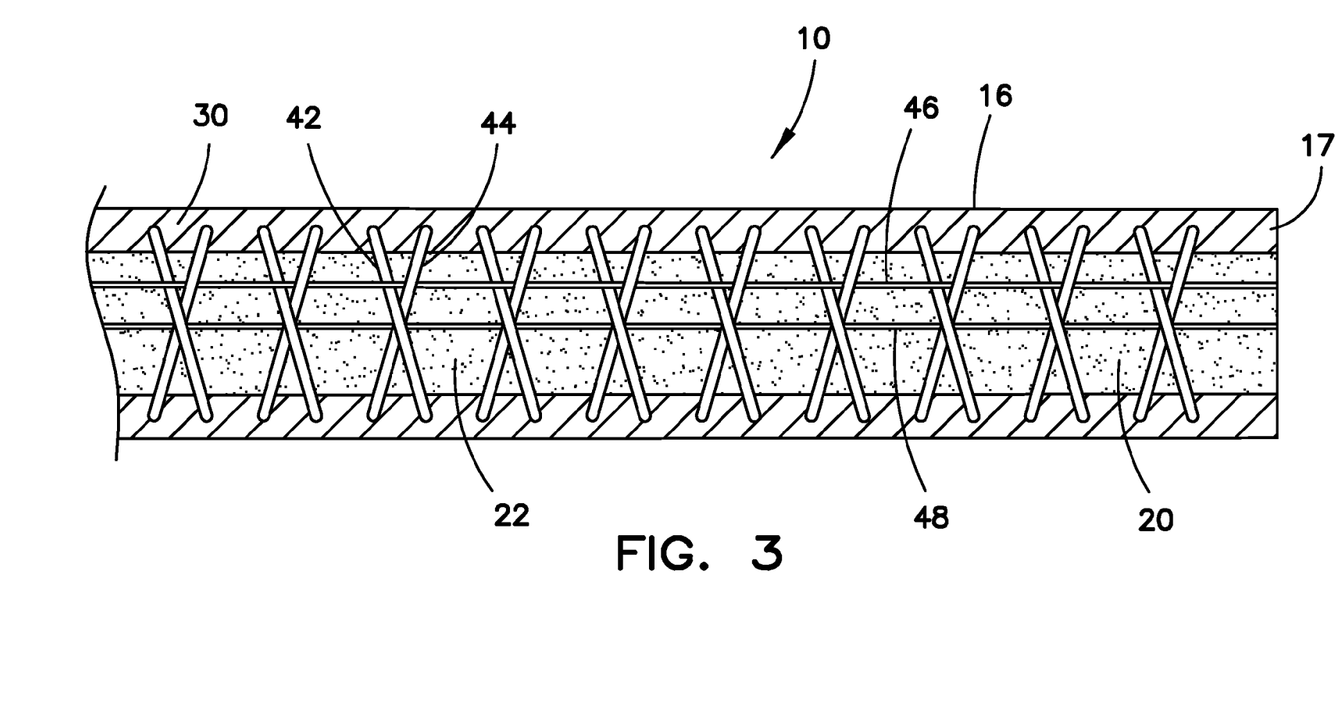
FIG. 3 is an enlarged longitudinal view, partially in section, of the distal portion of the sheath of FIG. 1.

In the example of FIGS. 1-3, a longitudinal sheath 10 includes a triaxial braid reinforcing member 40. FIG. 1 is a side view, partially in section, of the sheath 10. FIG. 2 is an enlarged longitudinal cross-sectional view of a portion of the wall of the sheath. FIG. 3 is an enlarged longitudinal view, partially in section, of the distal portion of the sheath of FIG. 1.

Introducer sheath 10 includes a tubular sheath body 12 having a passageway 13 extending longitudinally therethrough. Tubular body 12 includes a proximal portion 14, and a distal portion 16 alignable for initial insertion into the body passageway. In this non-limiting example, the proximal end of tubular sheath body 12 is received in a base structure 35, shown schematically in FIG. 1. Base structure 35 may be, for example, a handle, a manifold, a guiding catheter, etc. Those skilled in the art will appreciate that various other conventional proximal attachments and/or enclosures may be substituted. A reinforcing member 40 is disposed along the length of sheath body 12, in a manner to be described.

FIGS. 2 and 3 illustrate the layered structure of the sheath body. As illustrated, sheath body 12 comprises an inner liner 20, whereby the reinforcing member 40 is positioned over the inner liner. Reinforcing member 40 begins at or near the proximal end of the inner liner, and extends the majority of the length of the inner liner. Preferably, the reinforcing member stops short of the distal end 17 of the sheath, as shown in FIG. 3. Terminating the reinforcing member short of the distal end facilitates the ability to form a desired configuration (e.g., a distal taper) at a non-reinforced distal end portion by well-known means. Polymeric outer jacket 30 is mechanically connected to the outer surface 22 of inner liner 20 through the spaced strands, or filaments, of the reinforcing member 40.

Inner liner 20 preferably comprises a lubricious material. More preferably, the inner liner comprises a fluoropolymer of the type commonly used to impart strength and lubricity to a medical device, such as polytetrafluoroethylene (PTFE). Inner liners for sheaths are well known in the medical arts, and those skilled in the art can readily select an appropriate liner for a particular use. For example, materials such as high density polyethylenes (HDPE) or other polymers that may be modified by incorporating micronized PTFE are suitable inner liner materials.

It is envisioned that inner liner 20 can have a uniform inside diameter ranging up to about 12 mm (36 French), or even higher in some instances. The wall thickness of inner liner 20 will typically range between about 0.0254 mm and 0.076 mm (0.001 and 0.003 inch), and is preferably about 0.038 mm (0.0015 inch). Even larger, or smaller, wall thicknesses may be appropriate in a particular case. Those skilled in the art will appreciate that all dimensions recited herein are exemplary only, and that the device described herein may be constructed to be of any size necessary and appropriate to accomplish the purposes for which the sheath is to be utilized.

Preferably, the inner diameter of inner liner 20 is at least substantially uniform the entire length of passageway 13. Maintaining a substantially uniform inner diameter allows passage through the sheath of a medical interventional device having the largest possible outer diameter relative to the diameter of passageway 13. The lubricious inner liner material provides a slippery inner surface 21 to facilitate insertion and withdrawal of the medical interventional device. Inner surface 21 is preferably smooth and nonporous for minimizing the formation of blood clots and other thrombi thereon. The wall of the inner liner 20 should have sufficient radial rigidity to prevent the filaments of the reinforcing member from protruding into passageway 13.

As stated, outer jacket 30 is mechanically connected to the outer surface 22 of the inner liner 20 through the spacings of respective strands of the reinforcing member 40. Preferably, outer surface 22 of the inner liner 20 is chemically etched or mechanically roughened in well-known manner for enhancing the bonding between the liner and the outer jacket. Outer jacket 30 may be formed of any well-known polymer commonly used for such purpose. Preferably, outer jacket 30 comprises a heat formable material, such as a polyamide (nylon), a polyether block amide (PEBA), a polyurethane, or the like. As further described herein, this heat formable material melts upon heating, such that portions flow between the respective strands of the reinforcing member, and bond to the roughened outer surface 22 of the inner liner.

Various reinforcing members for medical devices are known in the medical arts. Typical reinforcing members comprise a helical coil or an interwoven braid configuration. In this example the reinforcing member comprises a braid, as further described herein. Braids utilized as reinforcing members in medical devices typically comprise strands interwoven in a biaxial pattern, i.e., wherein the interwoven strands are oriented in two different directions in a crisscross fashion. Examples of biaxial braids are illustrated, e.g., in U.S. Pat. No. 5,792,124 and U.S. Pat. Publ. No. 2010/0049168, incorporated by reference herein.

Those skilled in the art are aware that such braids may be formed by alternating a plurality of strands, e.g., three or more strands, in each direction in the criss-cross pattern, wherein a strand is intertwined over and under the other strands in the same construct with a uniform pattern and repetition. Each strand is often in a helical shape that alternates with the other strands in the construction. More complex braids may be multiple 8, 16, 24, 32, etc., strands that have equal numbers of strands formed or intertwined, wherein one-half of the strands form a right helix and one-half form a left helix. Interlacing is typically carried out in an over-under sequence, or alternating in a pattern such as, but not limited to, a two over, two under, or a one over, one under sequence in a helical fashion. Those skilled in the art are aware of other biaxial braided patterns in addition to those described.

As stated above, if high deployment forces are exerted by an interventional device, such as a stent, on the interior wall of a biaxial braided sheath as the stent is deployed through the sheath, the sheath is subject to elongation, or stretching. When elongation of a braid occurs, the diameter of the braid is reduced, thereby hindering, or preventing, deployment of the stent though the sheath. Those skilled in the art recognize that the presence of a biaxial braid offers little resistance to elongation.

Unlike the conventional biaxial braids described in the incorporated-by-reference patents, reinforcing member 40 in FIGS. 1-3 comprises a triaxial braid. In a triaxial braid, the respective strands of the braid are oriented in three different directions, rather than in two directions as in a conventional biaxial braid. As described herein, the triaxial braid has conventional strands woven in a generally biaxial pattern as described above, and additionally, has one or more strands running in a third direction. In this example, the one or more additional strands run axially, or longitudinally, relative to the biaxial strands, and are interwoven into the conventional braid structure. The presence of the longitudinal strands addresses the problems associated with conventional biaxial braids that provide less resistance to elongation. A triaxial braid having such longitudinal strands restricts, or hinders, the ability of the sheath to elongate upon exposure to high deployment forces. As a result, the sheath is able to maintain a sufficient inner diameter to enable deployment of the stent therefrom.

In the example shown in FIGS. 1-3, strands 42, 44 represent conventional interwoven strands of the type typically provided in biaxial medical braids. Longitudinal strands 46, 48 are interwoven into the reinforcing braided structure defined by strands 42, 44. As shown, longitudinal strands 46, 48 are interwoven in and out of strands 42, 44 along reinforcing member 40 in a generally uniform fashion, and are axial, or longitudinal, to the remaining portions of the braided structure defined by strands 42, 44. Although two longitudinal strands 46, 48 are shown in the figures, those skilled in the art will appreciate that other numbers of longitudinal strands (e.g., 1, 3, 4, etc) longitudinally positioned along the circumference of the sheath body may be utilized.

Triaxial braids are well known in the braiding art. Braiding machines capable of interweaving strands to form triaxial braids are commercially available, e.g., from Steeger USA, Inc., of Spartanburg, S.C. To date, however, use of triaxial braiding in the medical arts has been limited. The conventional helical braid strands (i.e., strands 42, 44) in the example shown in FIGS. 1-3 are preferably formed of a medical grade metal or metal alloy. Non-limiting examples of such materials include stainless steel, and shape memory alloys such as nitinol, a nickel-titanium alloy. Those skilled in the art will appreciate that strands 42, 44 may alternatively be formed of other medical grade materials known in the art to be suitable for such use, including, but not limited to, the polymers and composite materials listed below. Strands 42, 44 may be arranged with varied numbers, and pitches, of crossed wires, which number of strands and pitch may be varied within segments of a particular sheath, all in accordance with well known braiding techniques. As stated, braids are well-known reinforcements for medical devices, and those skilled in the art are well aware of suitable techniques for applying biaxial strands 42, 44 in a braided structure for medical applications.

Materials for longitudinal strands 46, 48 are selected to provide the desired properties of elongation resistance, tensile strength, and flexibility. Strands 46, 48 can generally be made from any nonmetallic, metallic, polymeric, synthetic compounds (organic or in-organic), composites (e.g., carbon fiber or glass), as well as other known biologically compatible materials capable of minimizing elongation yet maintaining flexibility in the medical device.

One example of a suitable material for longitudinal strands 46, 48 comprises fibers of an ultra high molecular weight polyethylene (UHMwPE), such as DYNEEMA® fibers. Such materials exhibit very high tensile strength with low elongation and weight, have low thermal properties and a relatively low coefficient of friction. Another suitable material comprises para-aramid synthetic fibers, such as poly-paraphenylene terephthalamide (KEVLAR®). Such materials exhibit high tensile strength with low elongation and weight, have good thermal and mechanical properties, and a relatively high coefficient of friction. Another suitable synthetic fiber comprises a meta aramid variant of the above, such as NOMEX® fibers. This material exhibits good strength with medium elongation and weight. It has excellent thermal properties and heat resistance, and a relatively high coefficient of friction. Still another suitable material comprises an organic polymer thermoplastic, such as polyether ether ketone (PEEK). PEEK exhibits good strength with relatively low elongation and weight. It has high thermal and mechanical properties, and a relatively low coefficient of friction. Those skilled in the art are believed capable of selecting a suitable composition in light of the present disclosure.

In one preferred embodiment, longitudinal strands 46, 48 will be formed of a more flexible material than that of strands 42, 44. Although high strength and a certain quantum of stiffness are generally desirable characteristics of strands 42, 44, it may be desirable in many, if not most, cases to form longitudinal strands 46, 48 from a more flexible composition than strands 42, 44. When it is intended to traverse curved body passageways with the sheath, the use of a stiff longitudinal strand material, such as stainless steel, may inhibit the ability of the sheath to bend along such passageways. Thus, for such uses, it is generally preferred to utilize a material for such strands that exhibits the desired properties of elongation resistance and tensile strength, and yet is not so stiff that it inhibits bending along the curved passageway. Conventional triaxial braiding machines are capable of weaving a braid having strands of different dimensions and compositions. Those skilled in the art are believed capable of selecting suitable materials based upon the intended use of the medical device.

Introducer sheath 10 may be formed to have any length required to fulfill its intended purposes. In most cases, the sheath will have a length between about 40 and 200 cm, and in some cases, may exceed 200 cm. In most cases, the sheath length will be between about 100 and 200 cm, such as 125 cm. Generally, the lengths of inner liner 20 and outer jacket 30 are the same. For an exemplary sheath of 100-200 cm length, the distal portion of the sheath (e.g., the distalmost 30-60 cm), may be covered with a conventional hydrophilic coating, such as AQ® hydrophilic coating. In addition, outer jacket 30 can comprise two or more discrete longitudinal segments of differing durometer along its length. Thus, for example, making the distal portion of the outer jacket from a lower durometer material than the material from which the proximal portion is made yields a tubular member 12 whose distal portion is more flexible than the proximal portion. This arrangement is described in greater detail in the incorporated-by-reference U.S. Pat. Publ. No. 2001/0034514.

An introducer sheath 10 according to the present invention may be constructed in the following manner. Initially, the inner liner 20 is placed on a suitably-sized mandrel. Generally, the mandrel will have an outer diameter substantially the same as the inner diameter of the inner liner to insure a close tolerance between the two. A triaxial braid as described above is cut to a length such that the braid will extend from the proximal end of the inner liner approaching the distal end of the inner liner. Preferably, the braid will extend about 90% of the length of the liner, or slightly more than this. The braid is slid over the liner at the proximal end of the mandrel. The slack is taken out of the braid in any known fashion so that the braid is taut over the liner. Those skilled in the art are aware of numerous suitable techniques for reducing or eliminating slack in an element, and which may be utilized herein. For example, the braid may be heat treated to a diameter smaller than the diameter of the mandrel at one end (such as the distal end), and stretched and tied off at the other end.

The outer jacket material 30 is then slid over the mandrel/liner/braid, and the entire assembly is placed in a conventional heat shrink enclosure. Heat shrink enclosures for use in forming medical devices are well known in the art, with fluorinated ethylene propylene (FEP) being one preferred composition for use herein. Those skilled in the art will appreciate that various alternative compositions for the heat shrink enclosure would also be suitable for use in forming this sheath, as long as the melt temperature of the material used for the outer jacket is lower than that of the heat shrink enclosure. The heat shrink enclosure and contents are placed in an oven and heated (typically at about 196° C. (385° F.) when FEP is used as the heat shrink and a polyether block amide is used as an outer jacket material) for a suitable period of time to melt the outer jacket material such that it flows between the braid strands and bonds with the roughened outer surface of the inner liner. After removal from the oven, the entire assembly is cooled. The FEP enclosure is then cut away and the mandrel is removed, both in well known fashion.

Other ways of bonding an outer jacket to an inner liner may be substituted for that described herein. For example, the outer jacket and the triaxial braid may be extruded together. In this process, the extruded jacket/braid is then slid over the inner liner/mandrel, and the heat shrink may be carried out as before. As another variation, the outer jacket itself may be the heat shrink material. In this event no separate heat shrink enclosure is necessary, and the heat is applied directly to the assembly allowing the outer jacket to melt and bond to the inner liner through the strands of the braid. No cutting or removal of the heat shrink enclosure is necessary in this variation.

The dimensions (for example, the thickness) of the various elements mentioned above should be selected in view of the proposed use of the introducer sheath 10. It is believed that the selection of such dimensions will lie within the level of skill in the art, once benefit of the present disclosure is had. While a modest amount of trial-and-error may be needed to obtain optimal dimensions, it is believed that any required experimentation will not be undue. Other details of constructions or composition of the various elements not otherwise disclosed are believed to be well within the ability of one of ordinary skill in the art. Further discussion and description of this process are provided, e.g., in the incorporated-by-reference patents.

Figure 4:
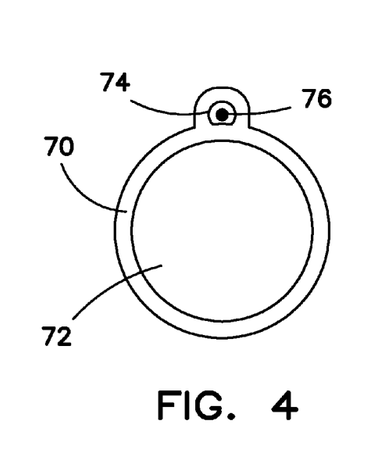
FIG. 4 is a cross-sectional view of an outer jacket prior to assembly into a sheath according to an embodiment of the invention.
Figure 5:
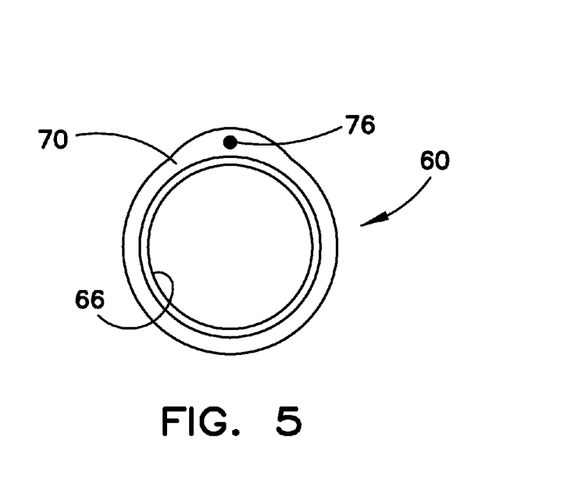
FIG. 5 is a cross-sectional view of a sheath according to an embodiment of the present invention.
Figure 6:
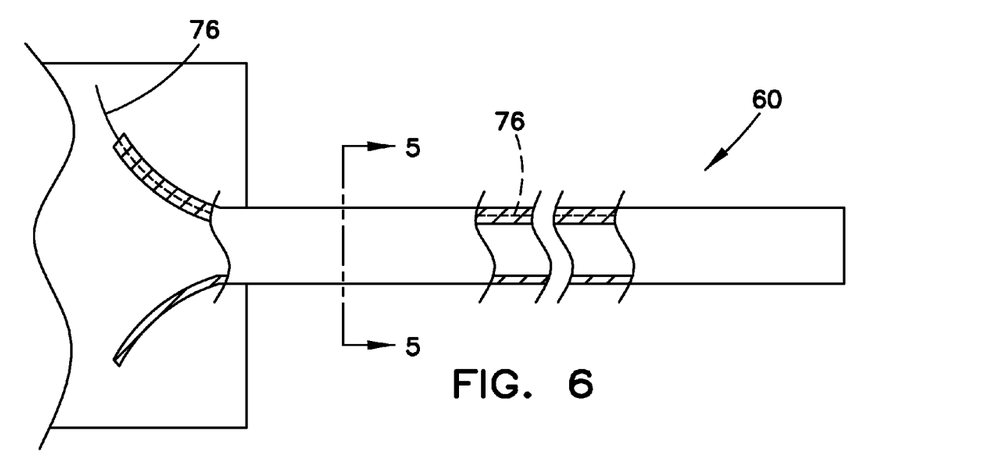
FIG. 6 is a side view, partially in section, of the sheath depicted in FIG. 5.

FIG. 6 illustrates another example of a longitudinally reinforced sheath 60. FIG. 4 is a cross-sectional view of the outer jacket 70 prior to assembly into sheath 60. FIG. 5 is a cross-sectional view of sheath 60.

As shown in FIG. 4, outer jacket 70 of this example includes dual lumens 72, 74. Dual lumen outer jacket 70 may be prepared in any conventional manner, such as via extrusion, and cut to a desired length. Preparing a dual lumen jacket as described is well within the level of ordinary skill in the art, and the skilled artisan is aware of suitable means for such construction. Larger lumen 72 of outer jacket 70 is sized to fit over a conventional inner liner 66 (FIG. 5), in the manner as described in the preceding example. Smaller lumen 74 is sized to receive a longitudinal reinforcing member 76. In one example, the smaller lumen may have a diameter of about 0.25 to 0.38 mm (0.010-0.015 inch). This lumen is favorably sized to receive a reinforcing member, such as a wire.

Sheath 60 may be better understood upon a description of its assembly. Longitudinal reinforcing member 76 is inserted or otherwise received in smaller lumen 74. Those skilled in the art will appreciate that the reinforcing member may be of any size and composition suitable for carrying out the desired application. With a smaller lumen 74 as described above, reinforcing member 76 may favorably comprise a 0.152 mm (0.006 inch) diameter wire of conventional construction as recited previously, e.g., stainless steel, nitinol, PEEK, UHMwPE, etc.

The proximal end of reinforcing member 76 may extend, e.g., about 5 cm beyond the proximal end of outer jacket 70. The distal end of the reinforcing member is preferably spaced (e.g., approximately 20 mm) from the distal end of the outer jacket. Spacing the distal end of the reinforcing member from the distal end of outer jacket 70 facilitates manufacture of the distal end of the resulting sheath (e.g., tapering or otherwise "tipping" the distal end of the sheath). In order to encapsulate the reinforcing wire and maintain it in a generally straight line along the axis of the jacket, the reinforcing wire will preferably remain in tension during the manufacture process as described below. This can be accomplished by initially melting the distal end of the jacket, e.g., via a heat gun, and capturing the distal end of the wire in the melted jacket portion. Tension may then be applied to the extended proximal end during assembly in any known manner, e.g., by capturing that end in a mechanism that engages the sheath and the system handle, and thereby shares the load applied by the handle.

Inner liner 66 is positioned on a suitably-sized mandrel. As stated above, the mandrel will generally have an outer diameter substantially the same as the inner diameter of the inner liner to insure a close tolerance between the two. Outer jacket 70 having reinforcing member 76 captured in lumen 74 as described above is slid over the mandrel/liner, and the entire assembly may be placed in a heat shrink enclosure as described above to bond inner liner 66 and outer jacket 70. During the heat shrink, the portions of sheath 70 surrounding smaller lumen 74 melt to form the generally annular configuration shown in FIG. 5. Typically, as the additional jacket material that defines lumen 74 melts, a greater wall thickness will result at that position of the jacket, as also shown in FIGS. 5 and 6. Following removal of the heat shrink enclosure, a flare may be formed in the proximal end if desired, e.g., by pushing the proximal sheath end over a heated tapered mandrel (flaring iron).

Inner liner 66 and outer jacket 70 may be formed of the same compositions as recited for the corresponding elements in the previous example. Although jacket 70 as shown in the example of FIG. 4 includes one smaller lumen 74, jacket 70 can be constructed to have other numbers of lumens 74 (such as 2, 3, or 4 lumens 74) circumferentially spaced along the outer diameter of jacket 70. Typically, when multiple lumens 74 are spaced along the diameter of jacket 70, there is a substantially equal spacing between adjacent lumens. Thus, such lumens may be spaced 180°, 120°, 90°, etc., apart along the outer circumference of jacket 70.

In another variation of the process described with reference to FIGS. 4-6, outer jacket 70 need not be extruded or otherwise prepared to define the one or more smaller lumens 74, such that the distal end of the reinforcing member 76 may be initially captured in the smaller lumen(s) as described in the above example. Rather, in this variation, one or more longitudinal reinforcing members 86 may be extruded or otherwise aligned for capture inside the elongated wall of the outer jacket 80 during formation of the jacket. In one preferred embodiment, longitudinal reinforcing member(s) are co-extruded during an extrusion of the outer jacket 80.

Figure 7:
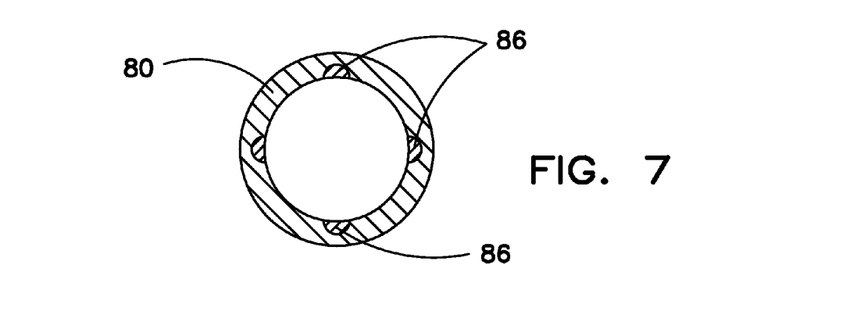
FIG. 7 is a cross-sectional view of a sheath outer jacket according to still another embodiment of the present invention.

One example of an outer jacket 80 having longitudinal reinforcing members 86 extruded therein is shown in FIG. 7. In this example, four separate longitudinal reinforcing members 86 are co-extruded with outer jacket 80. Those skilled in the art will appreciate that other numbers of reinforcing members may be extruded or otherwise received within the wall of the outer jacket 80 as desired. Preferably, the longitudinal reinforcing members are equally spaced along the circumference of the sheath. The composition of reinforcing members 86 may be selected in light of the intended use of the sheath. Typically, the artisan seeks to utilize a composition that is capable of providing the desired balance between longitudinal stiffness and radial flexibility of the sheath as described above. Non-limiting examples of reinforcing member compositions, and outer jacket compositions, have been provided hereinabove in the previous examples. In some embodiments, the reinforcing member may comprise a polymer having a greater stiffness than the stiffness of the outer jacket. This arrangement is believed to enhance bending flexibility of the sheath while tracking, while at the same time inhibiting an undesired stretching, or elongation, of the sheath during deployment. The selection of a suitable composition for a particular use, such as the compositions described hereinabove, is believed within the level of ordinary skill in the art when the principles disclosed herein are utilized.

During assembly of the sheath, outer jacket 80 having the reinforcing members extruded therein is slid over the mandrel having the liner positioned thereon, as described in previous examples (see, e.g., FIG. 5). The entire assembly may be positioned in a heat shrink enclosure, and baked in an oven for a designated time period to bond the outer jacket to the inner liner, as previously described.

Those skilled in the art will appreciate that additional variations in the heat shrink and bonding process for the examples of FIGS. 4-7 can be carried out as described above, and that other routine variations that may be carried out when forming the sheath. Further details of constructions or composition of the various elements of sheath, and further variations in its assembly not otherwise disclosed are believed to be within the ability of one of ordinary skill in the art.

It is therefore intended that the foregoing detailed description be regarded as illustrative rather than limiting, and that it be understood that it is the following claims, including all equivalents, that are intended to define the spirit and scope of this invention.

We claim:

1. A sheath for deploying a medical device to a target site in the body of a patient, comprising:
   a tubular liner having a proximal portion, a distal portion, and an outer surface; an outer jacket having a proximal portion, a distal portion, and an inner surface, said outer jacket positioned longitudinally around the liner such that the outer jacket inner surface is bonded to the outer surface of the liner; and
   a reinforcing member received within a length of the outer jacket, said reinforcing member extending along said outer jacket length and configured for inhibiting elongation of the sheath upon deployment of said device therefrom,
   wherein said reinforcing member comprises a triaxial braid encapsulated along said length of the outer jacket, and
   further wherein the triaxial braid comprises strands woven in two directions in a generally biaxial pattern, and one or more strands running in a longitudinal direction relative to the strands woven in the generally biaxial pattern and interwoven between the strands woven in the generally biaxial pattern,
   wherein the one or more strands running in the longitudinal direction are fixed to the outer jacket and/or the tubular liner and extend proximally from the proximal portion of the outer jacket, and
   wherein the sheath has an outwardly flared proximal end and the one or more strands running in the longitudinal direction extend proximally beyond the outwardly flared proximal end.

2. The sheath of claim 1, wherein said reinforcing member comprises a longitudinal stiffening wire encapsulated along said length of the outer jacket.

3. The sheath of claim 1, wherein the outer jacket comprises an extruded first polymer having a first stiffness, and the reinforcing member comprises a second polymer co-extruded along a length of the first polymer and encapsulated therein, the second polymer having a second stiffness greater than the first stiffness.

4. The sheath of claim 3, further comprising at least one additional longitudinal reinforcing member co-extruded along said length of the first polymer and encapsulated therein, said at least one additional reinforcing member having a stiffness greater than said first stiffness.

5. The sheath of claim 1, wherein the strands woven in the biaxial pattern have a greater stiffness than the one or more strands running in the longitudinal direction.

6. The sheath of claim 5, the one or more strands comprising a plurality of said strands running in said longitudinal direction, said strands being substantially equally spaced along a circumference of said outer jacket length.

7. The sheath of claim 6, wherein said reinforcing member extends about 90% of a length of said tubular liner.

8. A longitudinally reinforced sheath comprising:
   a tubular inner liner having a proximal portion, a distal portion, and an outer surface;
   a reinforcing element disposed along said outer surface of said inner liner, said reinforcing element comprising a triaxial braid, said triaxial braid disposed at said proximal portion of said inner liner and extending distally therefrom, wherein the triaxial braid comprises strands woven in two directions in a generally biaxial pattern, and one or more longitudinal strands interwoven with the strands woven in the generally biaxial pattern wherein the reinforcing element extends proximally from the proximal portion of the tubular inner liner; and
   an outer jacket positioned longitudinally around said reinforcing element, and connected to said inner liner, wherein the one or more longitudinal strands are fixed to the outer jacket and/or the tubular inner liner, and
   wherein the sheath has an outwardly flared proximal end and the one or more longitudinal strands extend proximally beyond the outwardly flared proximal end.

9. The sheath of claim 8, wherein said triaxial braid terminates proximal of a distal end of said liner.

10. The sheath of claim 8, wherein said triaxial braid extends along about 90% of a length of said inner liner.

11. The sheath of claim 8, wherein said inner liner comprises a lubricious fluoropolymer, and said outer jacket comprises a heat shrinkable polymer, said inner liner having a roughened outer surface wherein said outer jacket is bonded to said inner liner at said roughened outer surface.

12. The sheath of claim 8, wherein the strands woven in the generally biaxial pattern have a greater stiffness than the one or more interwoven longitudinal strands.

\* \* \* \* \*